(12) United States Patent
Bader

(10) Patent No.: US 6,337,629 B1
(45) Date of Patent: Jan. 8, 2002

(54) METHOD AND A SYSTEM FOR MONITORING A PERSON

(75) Inventor: Gaby Bader, Göteborg (SE)

(73) Assignee: Biosys AB, Gothenburg (SE)

( * ) Notice: Subject to any disclaimer, the term of this patent is extended or adjusted under 35 U.S.C. 154(b) by 0 days.

(21) Appl. No.: 09/540,902

(22) Filed: Mar. 31, 2000

(30) Foreign Application Priority Data

Sep. 14, 1999 (SE) ............................................. 9903270

(51) Int. Cl.[7] ............................................. G08B 23/00
(52) U.S. Cl. ...................... 340/576; 340/575; 600/484
(58) Field of Search ................................ 340/575, 576, 340/573.7, 573.1; 128/903; 600/508, 537, 595, 459, 483, 484, 502, 587, 301, 503

(56) References Cited

U.S. PATENT DOCUMENTS

| | | | |
|---|---|---|---|
| 4,569,536 A | 2/1986 | Tsuge et al. ................. 280/807 |
| 4,889,131 A | * 12/1989 | Salem et al. ................. 600/484 |
| 5,232,243 A | 8/1993 | Blackburn et al. .......... 280/732 |
| 5,311,197 A | 5/1994 | Sorden et al. ............... 342/457 |
| 5,474,327 A | 12/1995 | Schousek .................... 280/735 |
| 5,488,353 A | 1/1996 | Kawakami et al. .......... 340/576 |
| 5,511,553 A | * 4/1996 | Segalowitz .................. 600/508 |
| 5,515,858 A | * 5/1996 | Myllymaki ................... 600/483 |
| 5,612,876 A | 3/1997 | Zeidler et al. ................. 701/45 |
| 5,724,024 A | 3/1998 | Sonderegger et al. ........ 340/562 |
| 5,749,907 A | * 5/1998 | Mann .......................... 607/27 |
| 5,813,989 A | 9/1998 | Saitoh et al. ................ 340/576 |
| 5,846,206 A | 12/1998 | Bader .......................... 600/534 |
| 5,853,005 A | * 12/1998 | Scanlon ....................... 600/459 |
| 5,964,720 A | * 10/1999 | Pelz .............................. 600/595 |

FOREIGN PATENT DOCUMENTS

| | | |
|---|---|---|
| DE | 44 06 897 C1 | 5/1995 |
| EP | 0 560 351 A2 | 9/1993 |
| GB | 2289332 A | 11/1995 |
| WO | WO95/00368 | 1/1995 |

* cited by examiner

Primary Examiner—Van Trieu
(74) Attorney, Agent, or Firm—Nixon & Vanderhye P.C.

(57) ABSTRACT

In a method and a system the autonomic nervous system, and in particular parameters reflecting the current condition of the autonomic nervous system, are monitored for detecting a lower level of wakefulness. One such parameter, which has been found to indicate such a state, is cardiac oscillation. Thus, the autonomic nervous system affect the heartbeat of a person falling to sleep in such a way that the heartbeat will go through a series of acceleration and de-acceleration.

15 Claims, 3 Drawing Sheets

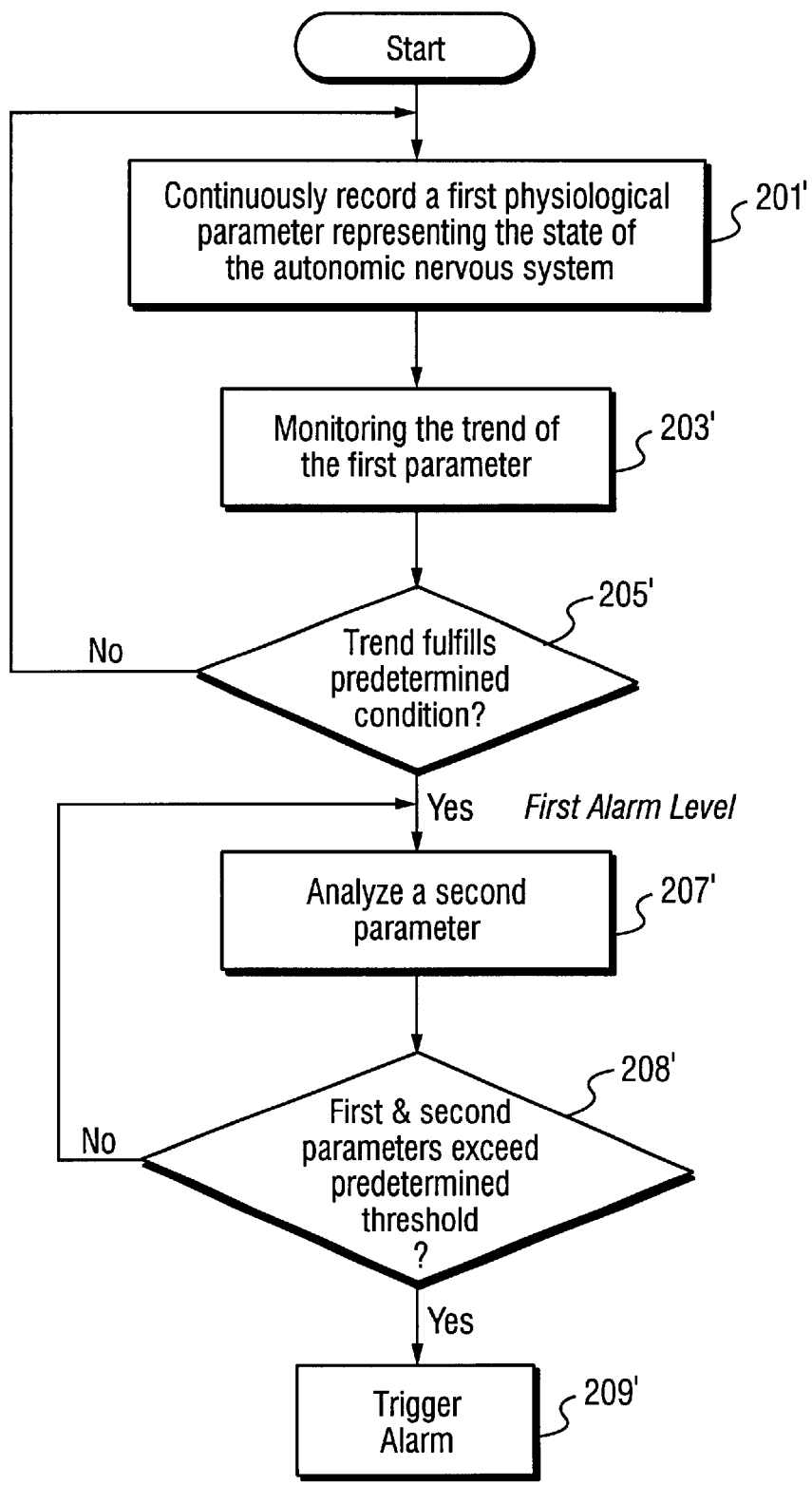

METHOD AND A SYSTEM FOR MONITORING A PERSON

TECHNICAL FIELD

The present invention relates to a method and a system for monitoring a person. In particular the present invention relates to a method and a system for monitoring drowsiness of a person performing a task where it is important to be awake, such as a person driving a car, monitoring personnel in a nuclear power plant or in a radar office, or a pilot.

BACKGROUND OF THE INVENTION AND PRIOR ART

In today's traffic, there is a problem relating to people driving vehicles despite the fact that they are too tired, sleepy or drowsy in order to safely drive their vehicle. In particular, during longer journeys, a person may start the journey in good shape and then as times goes being more and more drowsy, and, in the worst case, finally go to sleep. Such a scenario is of course highly undesirable, since it poses a great threat to both the driver and persons around him/her, such as other drivers or passengers in vehicles on the same road.

Also, it is known that when a person becomes drowsy, the eyelid and pupil movement pattern changes. Furthermore, in WO/33403 a method where the corresponding relationship between cardiac and respiratory functions are used in order to detect a condition of drowsiness.

SUMMARY

It is an object of the present invention to provide a method and a system, which have an improved reliability over the prior art. It is also an object of the present invention to provide a method and a system, which is more robust and user friendly compared to the methods according to the prior art.

This object is obtained by means of monitoring the autonomic nervous system, and in particular parameters reflecting the current condition of the autonomic nervous system. Thus, by means of intensive research it has been possible to show that it is in fact a change in state in the autonomic nervous system that causes the body to change certain patterns in, for example, eye movements. Thus, changes in activities in the autonomic nervous system are reflected by changes in behaviour of certain physiological parameters.

In a preferred embodiment the method and system comprise continuous recording of at least one parameter reflecting the current state of the autonomic nervous system, such as a parameter reflecting cardiac activity. If a trend in the monitored parameter fulfils a certain criteria or certain conditions, such as slowing down of the activity, a first alarm level is triggered by the system. At the first alarm level a second parameter reflecting the autonomic nervous system can be monitored in addition of the first parameter, such as body motor activity or respiratory activity. If both the monitored parameters exceed a pre-set threshold value an alarm is generated indicating that there is a risk that the person may fall to sleep. In this manner a multi-step threshold model is formed, which is used to indicate a potential risk of falling asleep.

When such an alarm is generated a number of different actions can be taken. For example, a light or sound signal can be generated, an air puff, or another change in the physical environment, or a vibrator located in the seat where the person is seated can be activated.

The invention relies on the fact that extensive studies have shown that the autonomic nervous system reflects the wakefulness level of a person. Thus, by monitoring a parameter, which reflects the current state of the autonomic nervous system, a lower level of wakefulness can be detected. One such parameter, which has been found to indicate such a state, is cardiac oscillation. Thus, the autonomic nervous system affect the heartbeat of a person falling to sleep in such a way that the heartbeat will go through a series of acceleration and de-acceleration.

BRIEF DESCRIPTION OF THE DRAWINGS

The present invention will now be described in more detail and with reference to the accompanying drawings, in which:

FIG. 3 is a more detailed flow chart.

DETAILED DESCRIPTION

Figure 1:
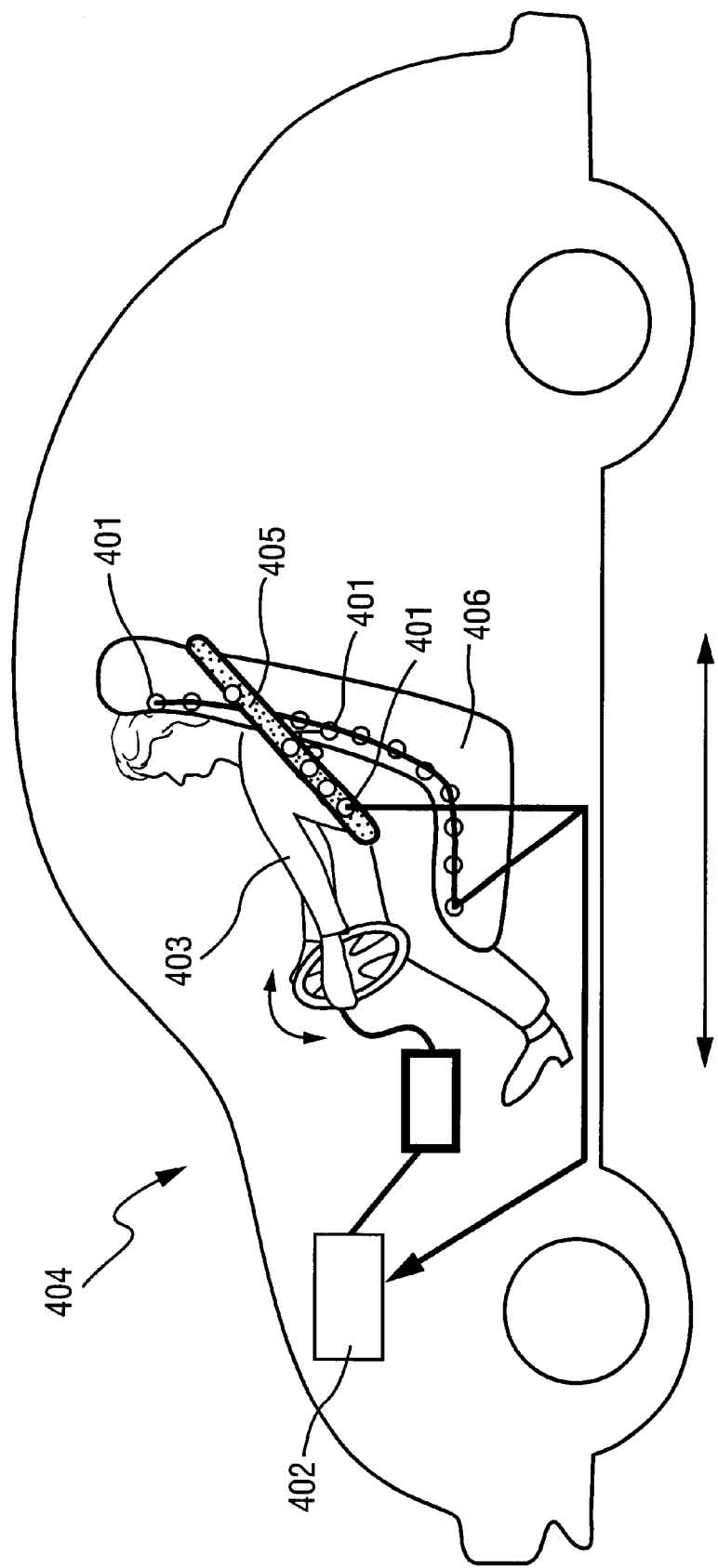
FIG. 1 is a general view of a person driving a car.

In FIG. 1 a driver 403 in a vehicle 404 is shown. In the vehicle 404 a seat 406 and a safety belt 405 are provided. The seat 406 and the safety belt 405 are provided with sensors 401. The sensors 401 are adapted to sense physiological parameters from a person, such as the driver 403, sitting in the seat 406.

For example, the sensors may output signals corresponding to respiration, cardiac activity and body movements from the driver. The sensors can be of any kind and are preferably of a conventional type, such as PVF type sensors. The sensors are connected to a data collecting computer unit 402. The unit 402 is operated by software, which uses the input data from the sensors for determining if the driver risk falling asleep. The procedure steps carried out in the unit 402 are described in more detail below in conjunction with FIG. 2.

The computer unit 402 is connected to an alarm-generating unit 407. The alarm unit can comprise several different alarm-generating devices. For example, the unit 407 can comprise a siren, a light emitting device, a vibrator etc. If the alarm unit is connected to a vibrator the vibrator can be located in the seat 406 or at some other suitable location. The object of the alarm unit is to indicate to the driver when he/she risks falling asleep, and thereby preventing that the driver become drowsy or falls asleep, which can have serious consequences. For example the alarm can activate the vehicle such as by means of slowing down the speed of the vehicle.

Figure 2:
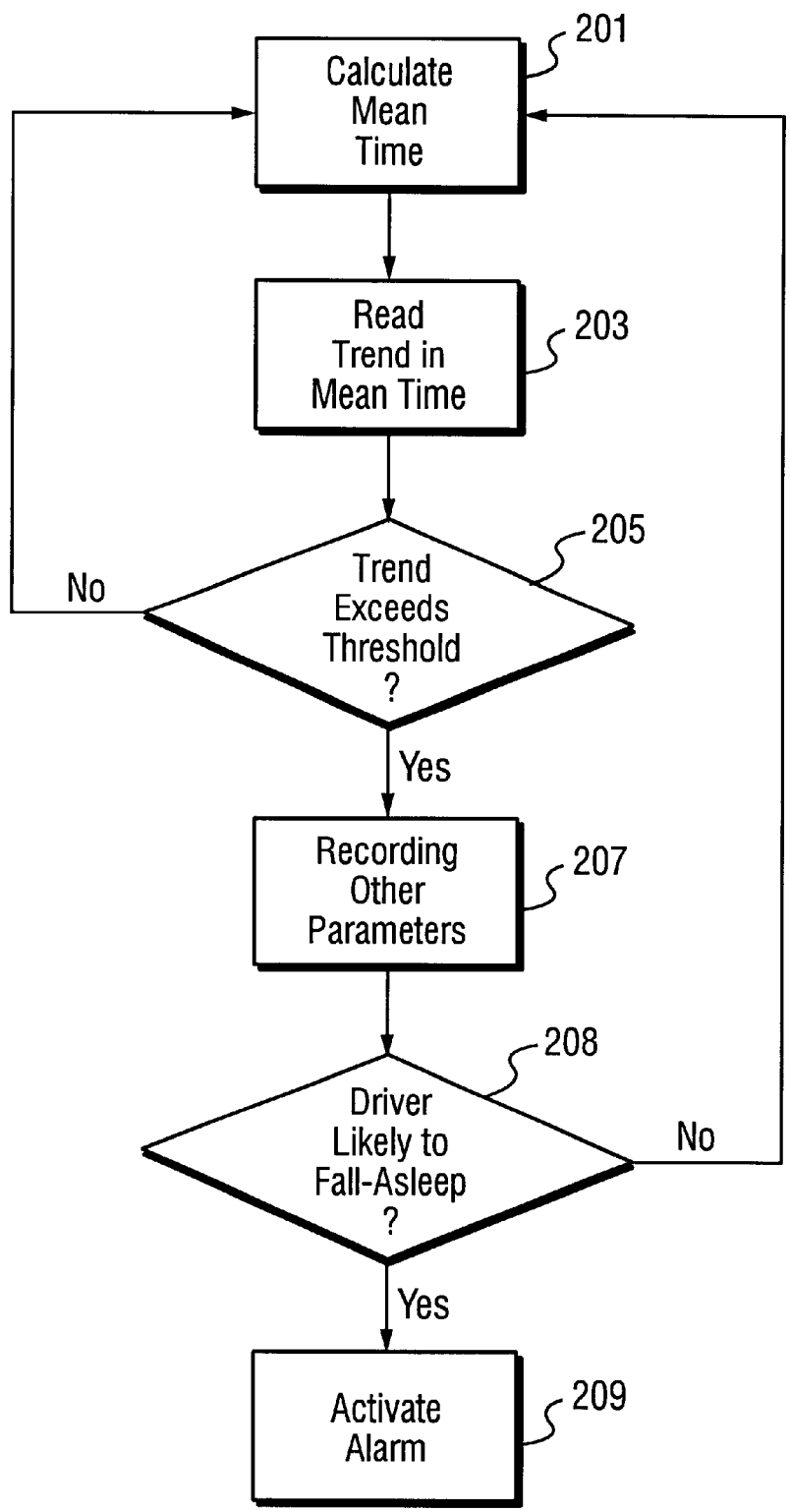
FIG. 2 is a flowchart illustrating different steps carried out when detecting a condition of drowsiness.

FIG. 2 and FIG. 3 show flowcharts illustrating different steps carried out by the software in the computer unit 402 for monitoring the driver 403 is shown. The software in the unit 402 continuously updates a first physiological parameter, such as a parameter corresponding to cardiac activity, and in particular the time interval between successive heartbeats.

In the case when the first physiological parameter monitored by the computer unit 402 is the time interval between successive heartbeats, the following process steps can be carried out by the software. First, in a step 201, 201', a mean value of the time between successive heartbeats during a first time interval window is calculated. The first window can have any duration, but in a preferred embodiment, the first time interval window is in the range of 1–20 seconds and in particular in the range of 5–10 seconds.

Next, in a step 203, 203', a trend in the mean value as calculated in step 201 is read. The trend can, for example, be derived by means of during a second time interval window, being longer than the first time interval window, and continuously recording the changes in the value obtained in the second window. The duration of the second window can for example be in the range 1–10 minutes, and in particular in the range 1–3 minutes. In the example given here the duration of the second window is 2 minutes and is updated every 6 second.

In the example given here, where cardiac activity continuously is recorded, the trend in the derived windowed mean value for successive heartbeats is monitored. If the trend exceeds one or several threshold values, the procedure continues to the step 207, and else the procedure returns to the step 201, as is indicated in the step 205, 205'.

The threshold value in step 203 can, for example, be set so that if the mean value between successive heartbeats is continuously increasing during a pre-set time interval, the threshold value is exceeded. Other possibilities for the threshold value include zero-crossing and slope values.

The object of setting the threshold value is to detect acceleration in cardiac activity, and in particular to detect a state of successive accelerations and de-accelerations. A pattern corresponding to successive accelerations and de-accelerations is used to indicate that the driver is falling asleep and in order to prevent this an alarm is triggered.

In order to prevent that a false alarm is triggered, the following additional process steps are preferably executed. In the step 207, 207' recording of one or several additional parameter(s) is activated. The additional parameter(s) can be additional physiological parameters, such as respiratory pattern (amplitude and frequency variations) or body motor activity, or other parameters. In the example described herein the additional parameters are physiological parameters. However, it is possible to record physical parameters as well. For example, the vehicle position on the road can be recorded or steering wheel movements can be recorded. Also, it is possible to adjust the alarm levels to different levels for different individuals, in order to further prevent triggering of an alarm at an incorrect time.

If the recorded additional parameters also indicate the same fact, i.e. that it is likely that the autonomic nervous system is in a state where the person is drowsy, the alarm generating unit is activated in a process step 209, 209'. The activation of the alarm is performed in order to indicate to the driver that there is a risk of falling asleep. If it is decided that the driver is not likely to fall asleep the process returns to the step 201 as is indicated in step 208.

The alarm generating unit can comprise audio and/or light signals, and means for generating environment conditioning signals. Also a vibrator can be located in the driver seat or the unit can trigger a change in temperature.

Use of the system and method as described herein achieves an improved monitoring of a person whom should stay awake and alert, such as for example a driver of a vehicle, a pilot or a person supervising an industrial process such as supervising personnel at a nuclear power plant. The system can be made very robust and insensitive to minor variations in the physiological parameters monitored by the system and used as input data to the method executing the steps for determining if the monitored person is drowsy or risks falling asleep. Thus, the system is adapted to prevent triggering a false alarm. Also, in order to even further ensure that the triggering of a false alarm is avoided, several parameters can be monitored, both physical and physiological, in the event that a first monitored parameter indicates that the alarm should be triggered. The logic for correlating the outcome of different monitored parameter can either be formed by different logic block or by one single logic block evaluating the combined signal from the different monitored parameters.

What is claimed is:

1. A method of monitoring the wakefulness condition of a person, comprising the steps of:

continuously recording at least a first physiological parameter representing the state of the autonomic nervous system, monitoring the trend of said at least first physiological parameter to detect whether the person is falling asleep, if the trend fulfils a certain pre-determined condition indicating the person is falling asleep, triggering a first alarm level and monitoring a second parameter different from the first parameter, and if the first physiological parameter in conjunction with the second parameter exceeds a pre-determined threshold indicating the person is falling asleep, triggering an alarm.

2. The method according to claim 1, wherein the predetermined threshold value comprises a multi-level threshold.

3. The method of claim 1 wherein the second parameter is a non-physiological parameter.

4. A method of monitoring the wakefulness condition of a human comprising the steps of:

continuously detecting the presence of successive accelerations and de-accelerations in the cardiac activity to detect whether the human is falling asleep, and in response to the detection of the presence of such successive accelerations and de-accelerations in the cardiac activity indicating the human is falling asleep, activating an alarm indicating the human is asleep or risks falling asleep.

5. The method according to claim 4, wherein respiratory and/or body movement patterns also are analyzed.

6. A system for monitoring the wakefulness condition of a person, comprising:

a recording unit that continuously records at least a first physiological parameter representing the state of the autonomic nervous system, a monitoring device that monitors a first trend of said at least first physiological parameter, and an analyzing unit that triggers a first alarm level and causes the monitoring device to provide at least a second parameter different from the first parameter, if the first trend fulfils a certain pre-determined condition indicating the person is falling asleep, and an alarm generating unit that triggers an alarm, if the first physiological parameter in conjunction with the second parameter exceeds a pre-determined threshold indicating the person is falling asleep.

7. The system according to claim 6, wherein the e unit comprises a multi-level threshold.

8. The system of claim 6 wherein the second parameter is a non-physiological parameter.

9. A system for monitoring the wakefulness condition of a human comprising:

an analyzing unit for continuously detecting the presence of successive accelerations and de-accelerations in the cardiac activity to detect whether the person is falling asleep, and an alarm unit arranged to activate an alarm indicating the human is asleep or risks falling asleep in response to the detection of the presence of such successive accelerations and de-accelerations in the cardiac activity.

10. The system according to claim 9, wherein respiratory and/or body movement patterns also are analyzed by the analyzing unit.

11. A method of detecting when the operator of a vehicle is about to fall asleep comprising:
   (a) monitoring at least one physiological characteristic of the operator;
   (b) analyzing a trend of the monitored physiological characteristic indicating loss of wakefulness;
   (c) conditioned on the results of the analyzing step, monitoring and analyzing a further characteristic associated with operation of the vehicle by the operator; and
   (d) conditionally attempting to wake up the operator in response to the results of steps (b) and (c).

12. The method of claim 11 wherein step (d) includes sounding an audible alarm.

13. The method of claim 11 wherein step (a) comprises monitoring steering movements of the vehicle.

14. The method of claim 11 wherein step (a) comprises monitoring position of the vehicle.

15. The method of claim 11 wherein step (a) comprises monitoring the operator's heart rate and step (b) comprises discerning the presence of successive accelerations/de-accelerations in the operator's heart rate.

* * * * *